United States Patent
Stinson

(10) Patent No.: US 7,004,962 B2
(45) Date of Patent: Feb. 28, 2006

(54) NEUROANEURYSM OCCLUSION AND DELIVERY DEVICE AND METHOD OF USING SAME

(75) Inventor: Jonathan S. Stinson, Plymouth, MN (US)

(73) Assignee: Schneider (USA), Inc., Maple Grove, MN (US)

( * ) Notice: Subject to any disclaimer, the term of this patent is extended or adjusted under 35 U.S.C. 154(b) by 0 days.

(21) Appl. No.: 09/852,541

(22) Filed: May 10, 2001

(65) Prior Publication Data

US 2001/0044629 A1 Nov. 22, 2001

Related U.S. Application Data

(63) Continuation of application No. 09/123,240, filed on Jul. 27, 1998, now abandoned.

(51) Int. Cl.
A61F 2/06 (2006.01)
(52) U.S. Cl. .................. 623/1.11; 623/1.12; 604/265
(58) Field of Classification Search ............... 623/1.11, 623/1.12; 604/265, 523, 525, 538, 263; 606/108, 191, 194, 195, 198, 200
See application file for complete search history.

(56) References Cited

U.S. PATENT DOCUMENTS

| | | | |
|---|---|---|---|
| 1,878,671 A | 9/1932 | Cantor | |
| 3,868,596 A | 2/1975 | Alfidi et al. | |
| 4,655,771 A | 4/1987 | Wallsten | |
| 4,705,517 A | 11/1987 | DiPisa, Jr. | |
| 4,710,192 A | 12/1987 | Liotta et al. | |
| 4,994,069 A | 2/1991 | Ritchart et al. | |
| 5,026,377 A | 6/1991 | Burton et al. | |
| 5,049,138 A | 9/1991 | Chevalier et al. | |
| 5,108,407 A | 4/1992 | Geremia et al. | |
| 5,108,420 A | 4/1992 | Marks | |
| 5,197,978 A | 3/1993 | Hess | |
| 5,201,757 A | 4/1993 | Heyn et al. | |
| 5,229,431 A | 7/1993 | Pinchuk | |
| 5,254,105 A | 10/1993 | Haaga | |
| 5,366,504 A | 11/1994 | Andersen et al. | |
| 5,382,261 A | 1/1995 | Palmaz | |
| 5,401,257 A | 3/1995 | Chevalier, Jr. et al. | |
| 5,423,849 A | 6/1995 | Engelson et al. | |
| 5,439,446 A | 8/1995 | Barry | |
| 5,451,235 A | 9/1995 | Lock et al. | |
| 5,484,444 A | 1/1996 | Braunschweiler et al. | |
| 5,486,193 A | 1/1996 | Bourne et al. | |

(Continued)

FOREIGN PATENT DOCUMENTS

DE 92 05 797 7/1992

(Continued)

OTHER PUBLICATIONS

*Peripheral Intervention: Products for Cardiology*, Cook Corporation, 6 pages.

(Continued)

Primary Examiner—Corrine McDermott
Assistant Examiner—Cheryl Miller
(74) Attorney, Agent, or Firm—Bingham McCutchen LLP

(57) ABSTRACT

A delivery device for delivering an implantable endoprosthesis with an occlusion region for occluding fluid flow to a desired location in a body lumen. The delivery device includes an outer sleeve and an inner tube terminating at a distal tip. The distal tip is made of one of a dissolvable, bioabsorbable, or deformable material. Upon deployment of the endoprosthesis at the desired location, the shape of the distal tip is altered to a different shape and withdrawn through the constricted region of the endoprosthesis.

40 Claims, 22 Drawing Sheets

U.S. PATENT DOCUMENTS

| | | | |
|---|---|---|---|
| 5,496,277 A | 3/1996 | Termin et al. | |
| 5,507,768 A | 4/1996 | Lau et al. | |
| 5,522,822 A | 6/1996 | Phelps et al. | |
| 5,527,338 A | 6/1996 | Purdy | |
| 5,562,698 A | 10/1996 | Parker | |
| 5,573,547 A | 11/1996 | LeVeen et al. | |
| 5,591,195 A | 1/1997 | Taheri et al. | |
| 5,603,698 A * | 2/1997 | Roberts et al. | 604/104 |
| 5,618,301 A | 4/1997 | Hauenstein et al. | |
| 5,628,788 A | 5/1997 | Pinchuk | |
| 5,634,936 A | 6/1997 | Linden et al. | |
| 5,656,036 A | 8/1997 | Palmaz | |
| 5,662,703 A | 9/1997 | Yurek et al. | |
| 5,679,470 A | 10/1997 | Mayer | |
| 5,690,644 A | 11/1997 | Yurek et al. | |
| 5,700,269 A | 12/1997 | Pinchuk et al. | |
| 5,709,703 A | 1/1998 | Lukic et al. | |
| 5,718,159 A | 2/1998 | Thompson | |
| 5,725,552 A | 3/1998 | Kotula et al. | |
| 5,762,625 A | 6/1998 | Igaki | |
| 5,830,217 A * | 11/1998 | Ryan | 606/108 |
| 5,902,333 A | 5/1999 | Roberts et al. | |
| 5,925,060 A | 7/1999 | Forber | |
| 5,925,074 A | 7/1999 | Gingras et al. | |
| 5,954,715 A | 9/1999 | Harrington et al. | |
| 5,984,964 A | 11/1999 | Roberts et al. | |
| 6,071,300 A * | 6/2000 | Brenneman et al. | 606/213 |

FOREIGN PATENT DOCUMENTS

| | | |
|---|---|---|
| WO | WO 9424961 | 11/1994 |
| WO | WO 95/24158 | 9/1995 |
| WO | WO 95/27448 | 10/1995 |
| WO | WO 96/01591 | 1/1996 |
| WO | WO 96/01599 | 1/1996 |

OTHER PUBLICATIONS

*Preliminary Investigation of the Irie Inferior Vena Caval Filter*, Thomas M. Vesely, M.D. et al., *Journal of Vascular and Intervention Radiology*, vol. 7, No. 4, pp. 529-535.

*Repositionable Vascular Occluder: Experimental Comparison with Standard Glanturco Coils*, Melhem J. A. Sharafuddin et al., *Journal of Vascular and Interventional Radiology*, Sep.-Oct. 1996, vol. 7, No. 5, pp. 695-703.

*Use of a Self-Expanding Vascular Occluder for Embolization During Endovascular Aortic Aneuryam Repair*, Noriyuki Kato et al., *Journal of Vascular and Interventional Radiology*, Jan.-Feb. 1997, vol. 1, No. 1, pp. 27-33.

U.S. Appl. No. 08/797,983 (now U.S. Pat. No. 5,919,224).
U.S. Appl. No. 08/904,467.
U.S. Appl. No. 08/905,806 (now U.S. Pat. No. 5,980,654).
U.S. Appl. No. 08/989,119.
U.S. Appl. No. 08/993,985.

* cited by examiner

DISTAL EXTREMITY OF CATHETER TUB

"DISTAL TIP MEMBER"

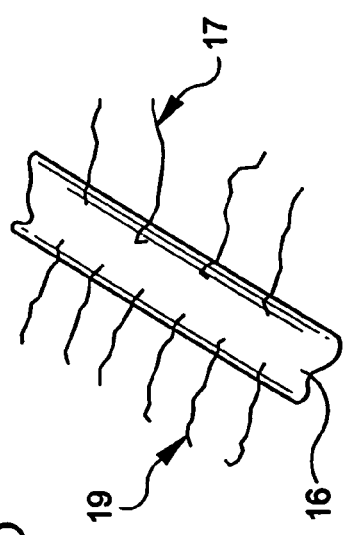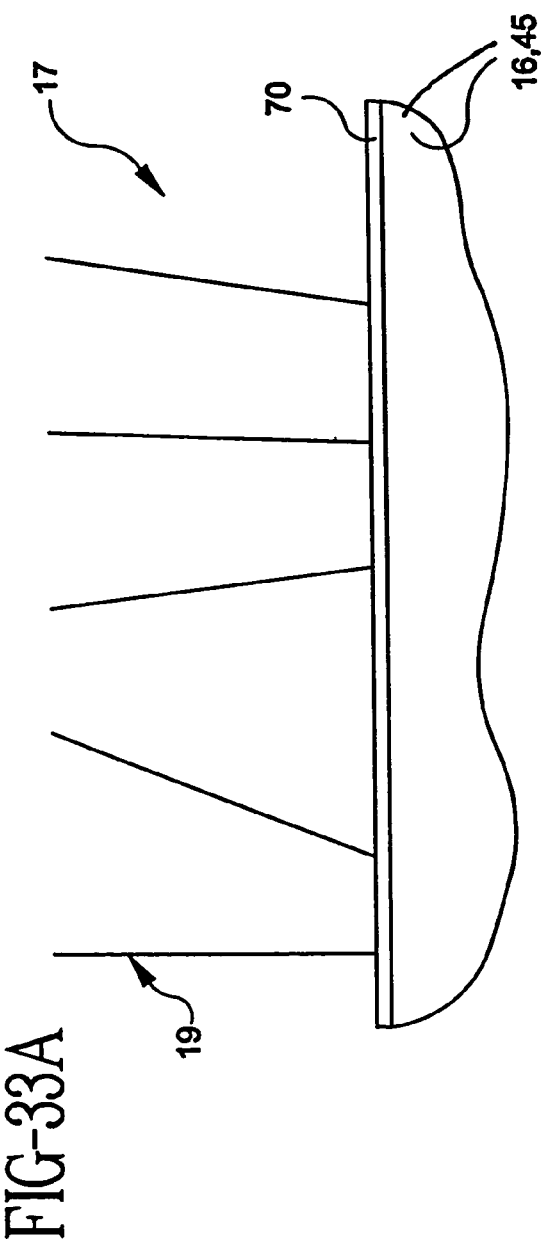
FIG-33
FIG-33A

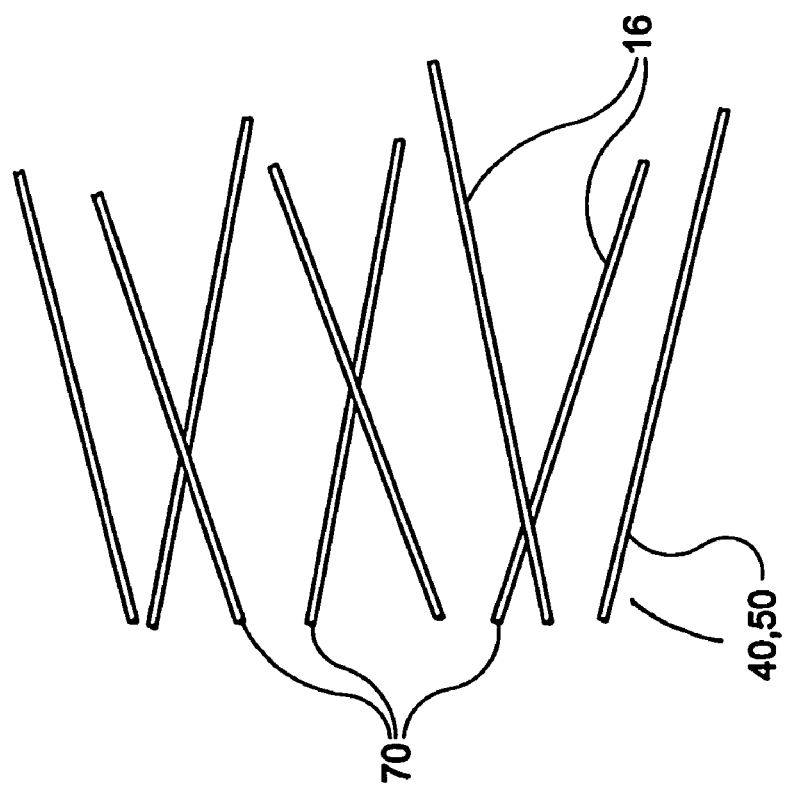
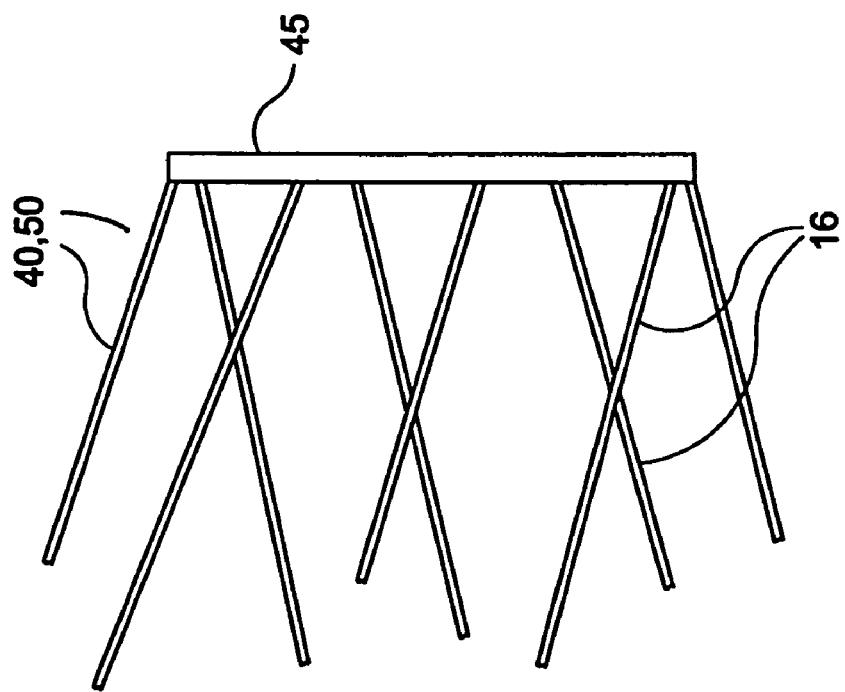

NEUROANEURYSM OCCLUSION AND DELIVERY DEVICE AND METHOD OF USING SAME

This is a continuation of application Ser. No. 09/123,240, filed Jul. 27, 1998, now abandoned.

FIELD OF THE INVENTION

The present invention relates to a braided endoprosthesis or occlusion device having a filament structure that transitions to a reduced diameter such as a cone-like shape. Occlusion material is disposed on portions of the filaments. The occlusion device is made of bioabsorbable or dissolvable material or metal material. The surface treatment enhances blood platelet adhesion and leads to thrombosis and lumen occlusion to prevent passage of blood and to exclude an aneurysmic vessel. The present invention also relates to a distal tip of a delivery device. The distal tip is made of a bioabsorbable or dissolvable material or a deformable material, or combination thereof.

BACKGROUND OF THE DISCLOSURE

Although there have been advances in cerebral aneurysm microsurgery, endovascular intervention is often necessary. Occlusion devices include detachable wire coils and microballoons or embolic agents such as cyanoacrylate. For example, the GDC coil system (Guglielmi Detachable Coil) is used to treat proximal and distal aneurysms in the carotid and vertebrobasilar arteries (Med Port, August–September 1997, 10 (8–9) p. 589–96, ISSN 0870-339X). The coils are pushed via a catheter to the implantation site and are detached from the end of the catheter to expand.

U.S. Pat. No. 4,655,771 (Wallsten) discloses a tubular stent with a diminishing end to act as a filter to trap emboli.

Bioabsorbable endoprostheses are disclosed in U.S. patent applications, entitled, "Bioabsorbable Self-Expanding Stent", Ser. No. 08/904,467 and "Bioabsorbable Implantable Endoprosthesis With Reservoir And Method Of Using Same", Ser. No. 08/905,806, each filed Aug. 1, 1997, and commonly assigned to the assignee of this application.

Another endoprosthesis is disclosed in U.S. patent application, entitled, "Stent-Graft With Bioabsorbable Structural Support", Ser. No. 08/993,985, filed Dec. 18, 1997, commonly assigned to the assignee of this application.

An occlusion device is disclosed in U.S. patent application, entitled, "Occlusion Device", Ser. No. 08/797,983, filed Feb. 12, 1997, commonly assigned to the assignee of this application.

A delivery device is disclosed in U.S. patent application, entitled, "Delivery Device For a Medical Device Having a Constricted Region", Ser. No. 08/989,119, filed Dec. 11, 1997, commonly assigned to the assignee of this application.

Other delivery devices are disclosed in U.S. Pat. No.: 5,026,337 (Burton et al.); U.S. Pat. No. 5,201,757 (Heyn et al.); U.S. Pat. No. 5,484,444 (Braunschweiler et al.); U.S. Pat. No. 5,662,703 (Yurek et al.); U.S. Pat. No. 5,690,644 (Yurek et al.), U.S. Pat. No. 5,709,703 (Lukic et al.); U.S. Pat. No. 5,700,269 (Pinchuk et al.); and U.S. Pat. No. 5,718,159 (Thompson).

All documents cited herein are incorporated by reference in their entireties for all purposes.

SUMMARY OF THE INVENTION

The invention relates to a generally self-expanding occlusion device which provides accurate placement, radiopacity, self-expansion, anchoring, and occlusion in one endoprosthesis. The occlusion device is a braided endoprosthesis with a straight-tubular portion and, preferably, a conical end portion. The straight-tubular portion of the device provides positioning and anchoring while the filaments on the conical end have a surface treatment such as thrombogenic agents or materials which is intended to cause occlusion of the artery that feeds the aneurysm. The occlusion device may include a member, at its diminished end, with a passage that allows the distal tip to pass through the occlusion device during withdrawal. An associated delivery system with a novel distal tip allows efficient deployment of the occlusion device.

The occlusion device is preferably constructed of biocompatible, radiopaque clad composite wire as described in U.S. Pat. No. 5,679,470 (Mayer). An alternate design includes biostable or bioabsorbable polymer filaments with attached radiopaque markers or biostable or bioabsorbable polymer filaments having compounded radiopaque agents therein for radiopacity purposes. An occlusion device made of a bioabsorbable material advantageously provides structural support and entraps thrombus long enough for the thrombus layer to grow into an endothelial seal. The occlusion device can subsequently be absorbed, leaving an implant-free vessel.

An opening in the distal end of the occlusion device is preferably as small as possible. The end of the tubular body or the distal tip must pass through the small opening of the occlusion device in order for the delivery system to be removed from the body. For a deformable polymer distal tip, the shape must be easily distorted to a smaller diameter and longer length when the distal tip is pulled against the edge of an attached member or opening in the occlusion device. The deformation of the distal tip may be elastic or inelastic (plastic). It is preferable that the distal tip profile is as large as the maximum profile of the delivery system during insertion and tracking through the vessel system to the treatment site. Once the occlusion device is implanted, the function of the distal tip is generally not required as the delivery system is retracted in the reverse direction relative to insertion.

In sum the invention relates to a delivery system including a tubular body having a proximal end, distal portion, a distal end on the distal portion, and a length between the distal end and the proximal end. The tubular body has a distal tip having a predetermined shape disposed on the distal portion of the tubular body. The distal tip includes at least a partially bioabsorbable or dissolvable material. The distal tip is adapted to be disposed in a body lumen and designed to at least partially dissolve or bioabsorb in vivo. The term "dissolve" means to degrade into individual constituents and the term "bioabsorb" means the degradation products are metabolized and utilized in normal biological bodily functions. The bioabsorbable material may include poly(vinyl pyrrolidone), methyl cellulose, carboxymethyl cellulose, cellulose derivative, or poly(ethylene oxide), colloidal hemicellulose gelatin, starch, or combinations thereof. The distal tip may include a lumen. The distal tip may include bioabsorbable or dissolvable material, biostable polymer and bioabsorbable or dissolvable composite material, biostable polymer core and bioabsorbable or dissolvable shell, biostable polymer shell and bioabsorbable or dissolvable core, porous biostable polymer matrix filled with a bioabsorbable or dissolvable material, or combinations thereof. The distal tip may dissolve or bioabsorb in less than 15 minutes. The distal tip may have a first dimension D prior to introduction into a body lumen and is configured to have one or more additional dimension D' ranging from about 0% to about 80% of the first dimension D after disposed in vivo. The distal tip may be configured to be in a first shape prior to placement in a body lumen and in one or more additional shapes when in vivo. The distal tip may have a greater average diameter in the first state than in the additional states. The delivery system may further include an occlusion device disposed on the tubular body. The occlusion device may be substantially proximal of the distal end of the distal tip and the tubular body may extend at least partially through the occlusion device. The distal tip may be configured to either bioabsorb or dissolve to one or more smaller profiles, or bioabsorb or dissolve substantially away. The distal tip may have a substantially smooth transition at an edge of the tubular body. The distal tip may be adapted to convert to a lower profile shape. The distal tip may include a deformable material. The distal tip may include one or more hollow, cavity, or porous portions to allow accumulation of bioabsorbable polymer acidic degradation products which would catalyze further degradation of the distal tip. For bioabsorbable polymers such as PLA and PGA, the degradation products are acidic and they will act upon the remaining polymer to catalyze the degradation reaction and increase the degradation rate. The distal tip may be molded or cast from a non-toxic, biocompatible material. The distal tip may degrade or bioabsorbs within a range of about 5 to about 10 minutes when in vivo.

The invention also relates to a delivery system including a tubular body having a proximal end, distal portion, a distal end on the distal portion, and a length between the distal end and the proximal end. A distal tip is disposed on the distal portion of the tubular body. The distal tip includes a deformable material adapted to deform when pressure is applied to at least a portion of the distal tip in vivo. The distal tip may have a first dimension D prior to introduction into a body lumen and have one or more additional dimensions D' ranging from 20% to about 80% of the first average diameter after disposed in vivo. The deformable material may include at least one elastic or plastic polymer. The elastic polymer may include at least one of silicone, polyurethane, polycarbonate urethane, polybutylene, PTFE, ePTFE, polyethylene, or combinations thereof. Elastic deformation is defined by the tip springing back to nearly its original shape after being pulled through the opening at the end of the occlusion device. Plastic deformation is defined by the distal tip remaining permanently deformed as it is pulled through and out of the occlusion device. The limit upon plastic deformation is that the distal tip material cannot be strained so far as to result in fracture. The distal tip may include one or more hollow, cavity, or porous portions to enhance deformability by allowing the open spaces or voids to accommodate material collapse when pressure is applied. The tubular body may further associate with an outer tubular body to constrain an associated implantable endoprosthesis.

The invention also relates to a method of using a delivery device including: providing a delivery device having a tubular body including a proximal end, distal portion, a distal end on the distal portion, and a length between the distal end and the proximal end. A distal tip is disposed on the distal portion of the tubular body. The distal tip includes at least one of a dissolvable, bioabsorbable or deformable material. A medical device is associated with the distal tip and is positioned on the distal portion of the tubular body; inserting the delivery device into a body lumen; advancing the delivery device to a desired location within the body lumen; deploying the medical device in the body lumen; and allowing at least a portion of the distal tip to at least one of deform, dissolve or bioabsorb to a lower profile prior to withdrawing the delivery device from the body lumen. The method may further include withdrawing the distal end of the tubular body through at least a portion of the medical device after the medical device has been deployed in a body lumen.

The invention also relates to an occlusion device including a first set of filaments each of which extends in a configuration along a center line and having a first common direction of winding. The occlusion device also includes a second set of filaments each of which extends in a configuration along a center line of the occlusion device and having a second common direction of winding. A structural support system may be formed by the first set of filaments and the second set of filaments. The structural support system includes a proximal end, distal end, one or more outside diameters and inside diameters, inside surface and outside surface. At least one thrombogenic treatment including at least one of a coating, fuzz, or fibers is disposed on at least a portion of one or more filaments. The thrombogenic treatment is intended to cause thrombosis and vessel occlusion. The structural support system may have a diminishing diameter on at least one end. The occlusion device may include an attached member having an inside diameter and outside diameter. The member may have a lumen therein. The thrombogenic treatment is not intended to significantly inhibit the movement of wires at wire cross-over points in the braid as the endoprosthesis is radially and axially flexible. Preferably, thrombogenic treatment is selectively applied to areas other than the filament cross-over points or by selecting a thrombogenic treatment that is generally highly elastic. The structural support system may have a shape that is cone-like, elliptical-like, cylindrical-like, trumpet-like or funnel-like. The member may be configured to prevent snagging of filaments. The member may be made of Elgiloy®, biostable polymer material or a bioabsorbable polymer material. The member may be a substantially continuous ring on at least one end of the structural support system. The thrombogenic treatment may substantially encapsulate a plurality of ends of the filaments. The filaments may have an average diameter of from about 0.0254 mm to about 0.7 mm. The filaments may include: 1) a metal with spring characteristic properties including Elgiloy®, 304 stainless steel, 316 stainless steel, or nitinol; 2) a polymer with a generally high Young's Modulus and yield strength including PET or nylon; 3) a bioabsorbable polymer including (PLLA), poly-D-lactide (PDLA), polyglycolide (PGA), polydioxanone, polycaprolactone, polygluconate, polylactic acid-polyethylene oxide copolymers, modified cellulose, collagen, poly(hydroxybutyrate), polyanhydride, polyphosphoester, poly(amino acids), or related copolymer materials and combination thereof; and 4) a metal with a generally high ductility and generally low to moderate yield strength including annealed stainless steel, platinum, gold, tungsten, or tantalum.

The tubular body with a bioabsorbable distal tip or an elastic or plastic deformable distal tip may advantageously be used in an endoluminal delivery system during an interventional procedure to penetrate tight or tortuous strictures, valves, or orifices. The distal tip having a capability to obtain a reduced profile advantageously allows efficient retrieval. Examples of an interventional procedure include placement of an endoprosthesis in a curved vessel, such as in the carotid artery and colon; valvoplasty where a filter, stent, artificial or natural valve or occlusion implant is delivered past a venous valve; and implantation of a stent-graft in an aortic aneurysms.

Still other objects and advantages of the present invention and methods of construction and use of the same will become readily apparent to those skilled in the art from the following detailed description, wherein only the preferred embodiments are shown and described, simply by way of illustration of the best mode contemplated of carrying out the invention. As will be realized, the invention is capable of other and different embodiments and methods of construction and use, and its several details are capable of modification in various obvious respects, all without departing from the invention. Accordingly, the drawings and description are to be regarded as illustrative in nature, and not as restrictive.

BRIEF DESCRIPTION OF THE DRAWINGS

FIGS. 32–34 are schematic views of thrombogenic material and coating on the filaments;

FIGS. 34–40 are cross-sectional schematic views of embodiments of the distal tip having hollow cavity or porous portions;

FIG. 41 is a schematic view of a deployed occlusion device with a member; and

FIG. 42 is a schematic view of a deployed occlusion device with coatings on ends of the stent element.

DETAILED DESCRIPTION OF THE INVENTION

Figure 1:
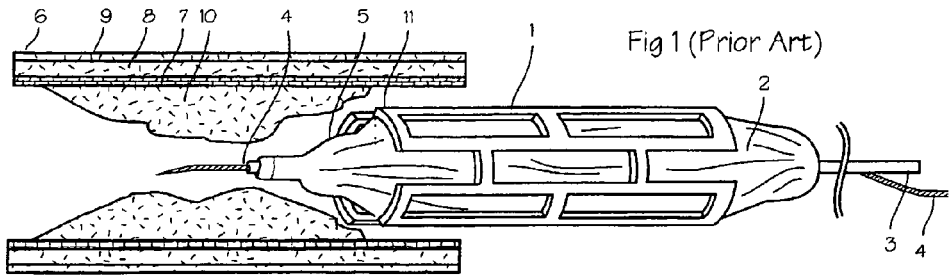
FIG. 1 is a schematic view of a prior art embolization coil at an aneurysm.

Reference is made to FIG. 1 showing a prior art embolization coil 6 at an aneurysm 5. The embolization coils 6 are implanted in a vessel to occlude an aneurysm 5.

Figure 2:
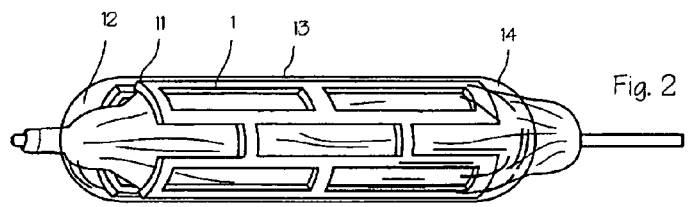
FIG. 2 is a schematic view of an occlusion device in a body lumen.

Shown in FIG. 2 is an illustration of an endoprosthesis 40 or occlusion device 50 of the present invention after deployment in a body lumen. The occlusion device 50 is preferably made of radiopaque Halo™ wire filaments or bioabsorbable filaments. The filaments 16, 17 may be mono-filament or multi-filament.

An occlusion device 50 made of bioabsorbable filaments 16, 17 may substantially degrade in vivo in from about 1 year to about 2 years. "Substantially degrade" means that the occlusion device 50 has lost at least 50% of its structural strength. It is preferable that the bioabsorbable occlusion device 50 lose about 100% of its structural strength and mass. Filaments 16, 17 made of polyglycolide may substantially degrade in vivo in a time of from about 3 months to about 1 year. Filaments 16, 17 may be made of polygluconate, polydioxanone, or combinations thereof and substantially degrade in vivo in from about 1 week to about 3 months. Filaments 16, 17 may be substantially homogeneous in cross section and length. A thrombus 60 is shown formed in the occlusion device 50.

Figure 3:
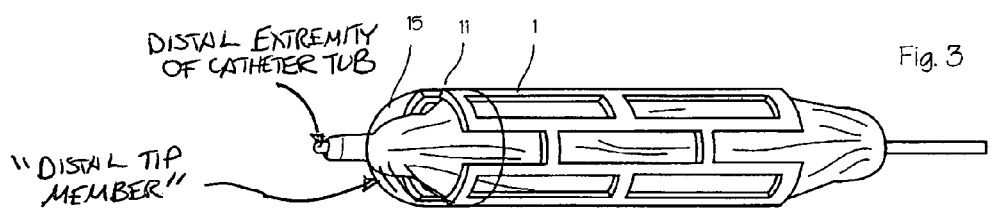
FIG. 3 is a schematic view of an occlusion device fully constrained on delivery system.

FIG. 3 illustrates an endoprosthesis 40, 50 fully constrained on a delivery system 8. The endoprosthesis 40 or occlusion device 50 preferably overlaps the proximal end 20A of the distal tip 20. The delivery system 8 includes a collapsible, deformable, or dissolvable distal tip 20 that is in an expanded state during passage through the vessels and is in a generally smaller state during withdrawal through the occlusion device 50.

A method of use of a delivery system 8 includes providing a delivery system 8 having a distal tip 20 disposed on the distal portion of the tubular body 10. The distal tip 20 includes at least one of a dissolvable, bioabsorbable or deformable material. A medical device 40, 50 is associated with the distal tip 20 and is positioned on the distal portion of the tubular body 10. The delivery system 8 is inserted into a body lumen, advanced to a desired treatment location, and the medical device 40, 50 is deployed in the body lumen. A portion of the distal tip 20 is deformed, dissolved, or bioabsorbed to a lower profile and the distal tip 20' is then withdrawn from the body lumen. The distal end of the tubular body 10 may be withdrawn through at least a portion of the medical device 40, 50 after the medical device 40, 50 has been deployed in a body lumen.

Figure 4:
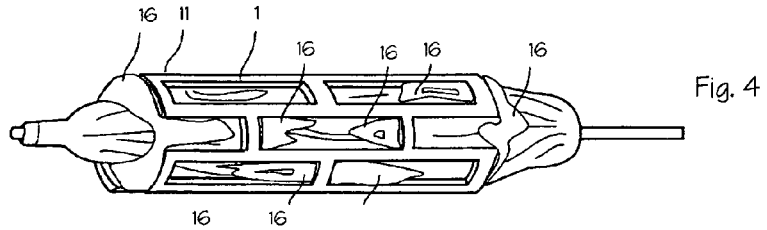
FIG. 4 is a schematic view of an occlusion device partially deployed.

FIG. 4 illustrates partial deployment of an occlusion device 50. Also shown is an exterior tube 15 that is used to constrain the occlusion device 50 on the tubular body 10. A distal tip 20 is generally larger than the distal opening in the occlusion device 50, prior to insertion of the distal tip 20 into a body lumen.

The distal tip 20 is preferably manufactured separately from the tubular body 10 and is subsequently attached to the tubular body 10 or to other components of the delivery system 8. A preferred method of attachment includes adhering the distal tip 20 to the tubular body 10. The distal tip 20 may be adhered to the tubular body 10 by means of an ultraviolet light curing adhesive, such as Sicamet, or an air curing adhesive such as cyanoacrylate. The adhesive can be applied to the surfaces of the parts 10, 20 and an end-to-end or butt-joint may be formed therebetween. A seam of adhesive can be deposited around the circumference of an edge of the distal tip 20 and on the surface of the tubular body 10 and pressure can be applied to join the two parts.

Another method to join the parts includes applying the adhesive to a least one of the surface of the tubular body 10 or the inner surface of the distal tip 20 and then sliding the distal tip 20 onto the end of the tubular body 10. This method may be used with a sufficient gap between the outside diameter of the distal tubular body 10 and the inside diameter of a lumen in the distal tip 20. As an alternative, the distal tip 20 can be made by injection molding and can be attached to the tubular body 10 during the molding process. An end of the tubular body 10 can be inserted into the mold cavity and the cavity can be filled with the desired material chosen for the distal tip 20. The distal tip 20 may also be attached by ultrasonic or fusion welding. A smooth transition at the intersection of the distal tip 20 and the inner tube 10 may be obtained by surface treatment or grinding of the parts. The preferred material for the tubular body 10 is a polymer material such as PEEK (polyether ether ketone). Other materials could include polyethylene, nylon, or PET (polyethylene terepthalate).

Figure 5:
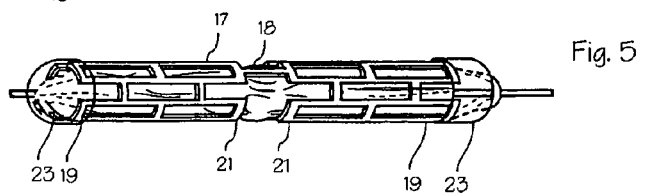
FIG. 5 is a schematic view of a deployed occlusion device and the distal tip partially deformed, dissolved or bioabsorbed.

FIG. 5 illustrates a deployed occlusion device 50 and a distal tip 20'. The distal tip 20' is shown partially deformed, dissolved or bioabsorbed to a lower or smaller profile. The shape of the distal tip 20' is of sufficient size to pass through an opening at the distal end of the occlusion device 50.

Figure 6:
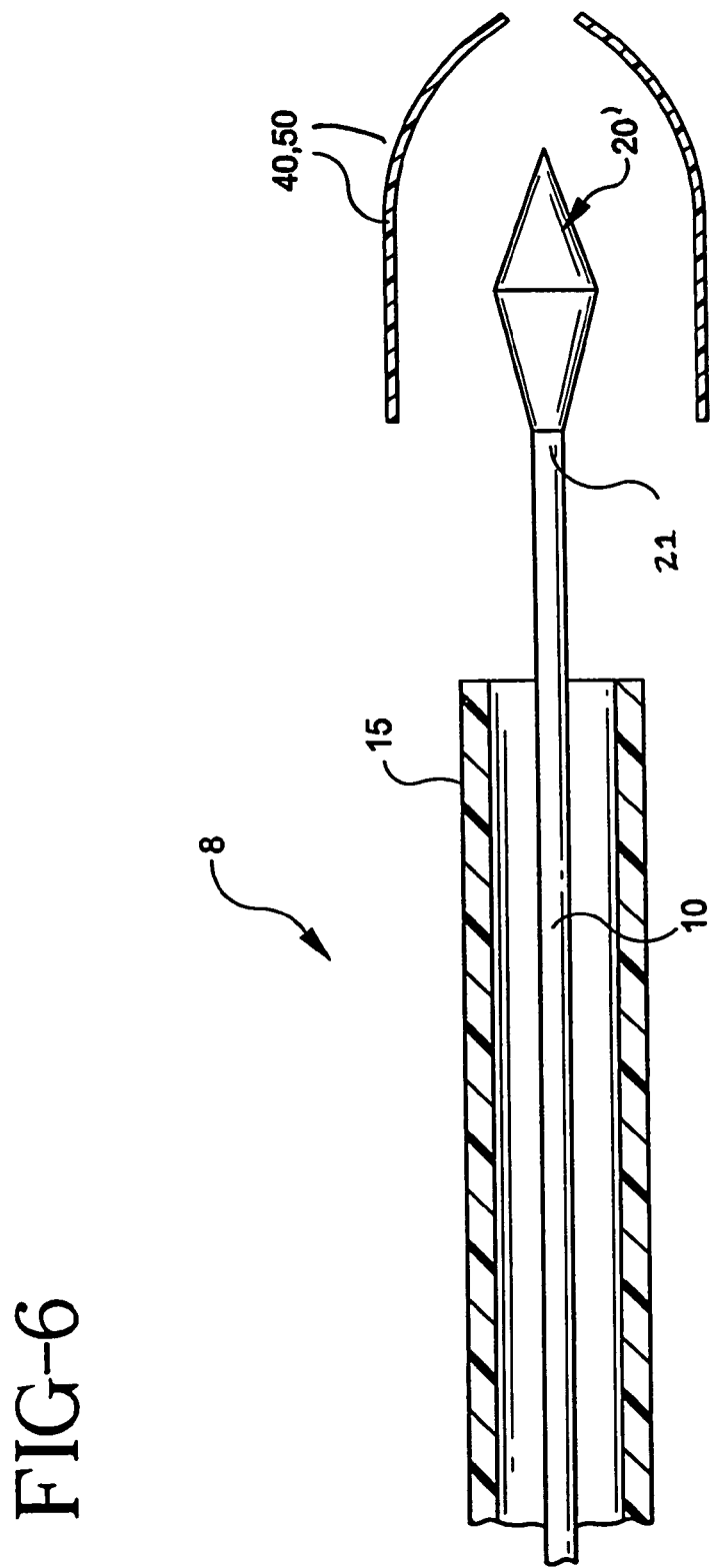
FIG. 6 is a schematic view of a deployed occlusion device with the distal tip proximal of the distal end of the occlusion device.

FIG. 6 illustrates a distal tip 20' that has been withdrawn in a proximal direction through an opening at the distal end of a deployed occlusion device 50.

Figure 7:
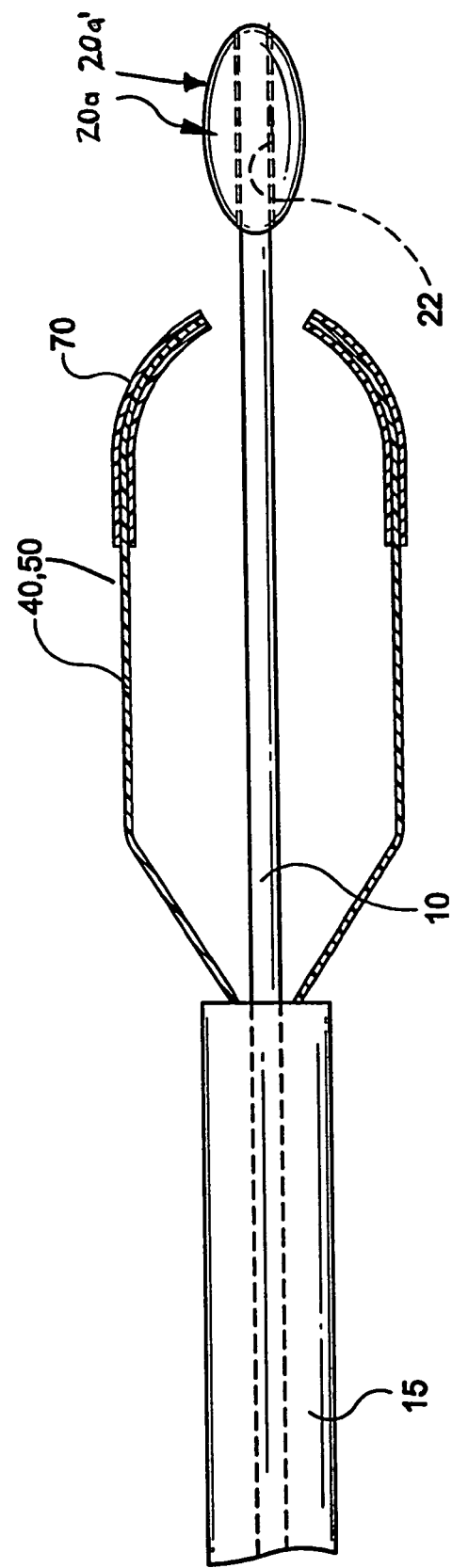
FIG. 7 is a schematic view of a partially deployed occlusion device and a distal tip.

FIG. 7 is a schematic view of a deployed occlusion device 50 and a distal tip 20, 20' having a generally elliptical or tear-drop shape. The distal tip 20 may be made into various predetermined shapes including a diamond-like shape. In one preferred embodiment, the distal tip 20 is made of a bioabsorbable or dissolvable material that at least partially dissolves or bioabsorbs in vivo. The bioabsorbable material may include poly(vinyl pyrrolidone), methyl cellulose, carboxymethyl cellulose, cellulose derivative, or poly(ethylene oxide), colloidal hemicellulose gelatin, starch, and combinations thereof. The distal tip 20 preferably includes a lumen 22. The distal tip 20 may be made of a bioabsorbable or dissolvable material, biostable polymer and bioabsorbable or dissolvable material composite, biostable polymer core and bioabsorbable or dissolvable shell, biostable polymer shell and bioabsorbable or dissolvable core, porous biostable polymer matrix filled with a bioabsorbable or dissolvable material, or combinations thereof. Once the distal tip 20 is in vivo, the outside original dimension D converts to one or more additional dimensions D' ranging from about 0% to about 80% of the original dimension D. The distal tip 20 bioabsorbs or dissolves to one or more smaller profile states, or bioabsorbs or dissolves substantially away. A dissolvable distal tip 20 could be made by molding or casting the shape from a non-toxic, biocompatible material that degrades by the constituents of blood within about 5 to 10 minutes of exposure. The bioabsorbable distal tip 20 may include hollow, cavity, or porous portions to enhance degradation.

In another preferred embodiment, the distal tip 20 is made of an elastic or plastic deformable material which deforms when pressure is applied to a portion of the distal tip 20 in vivo. The distal tip 20 has an original dimension D prior to introduction into a body lumen and has one or more additional dimensions D' ranging from 20% to about 80% of the original dimension after disposed in vivo and pressure is applied when withdrawn proximally against the occlusion device 50 or a member 45. The length of the deformable distal tip 20 generally increases as deformation occurs. The deformable tip 20 may be made from a polymer material that squeezes through a reduced size space. The polymer may include silicone, polyurethane, polycarbonate urethane, polybutylene, PTFE, ePTFE, polyethylene, or combinations thereof. The deformable distal tip 20 may include hollow, cavity, or porous portions.

Figure 8:
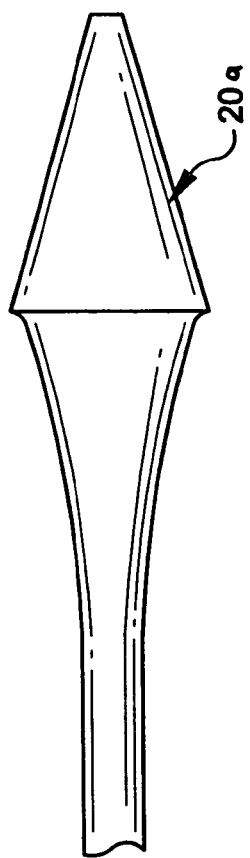
FIGS. 8–13 are schematic side views of embodiments of the distal tip.
Figure 9:
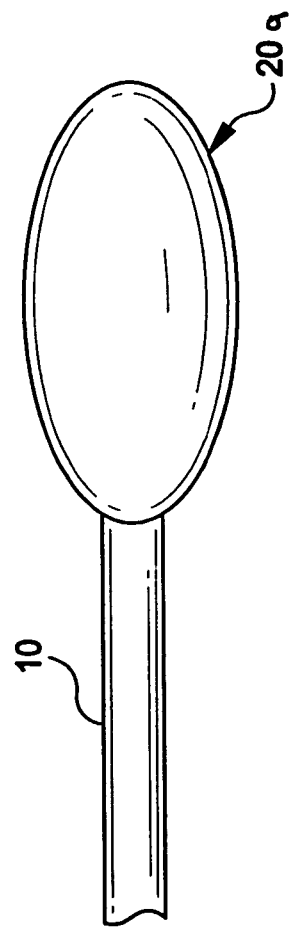
Figure 10:
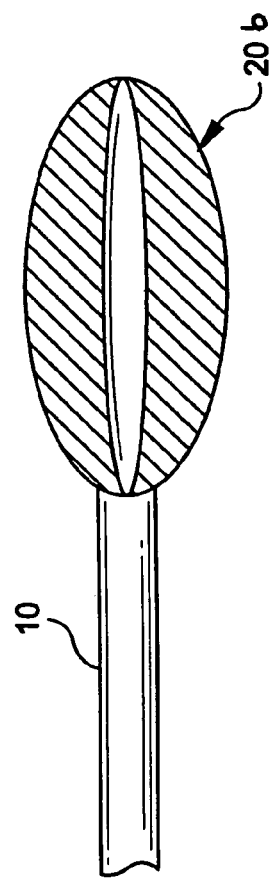
Figure 11:
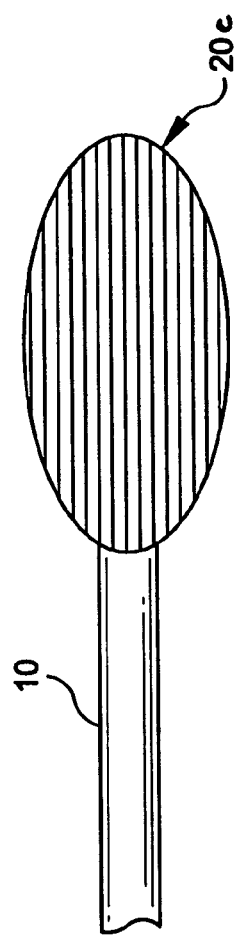
Figure 12:
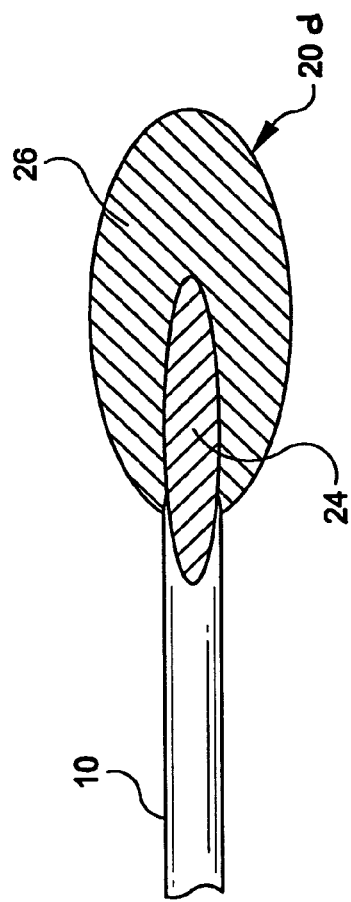
Figure 13:
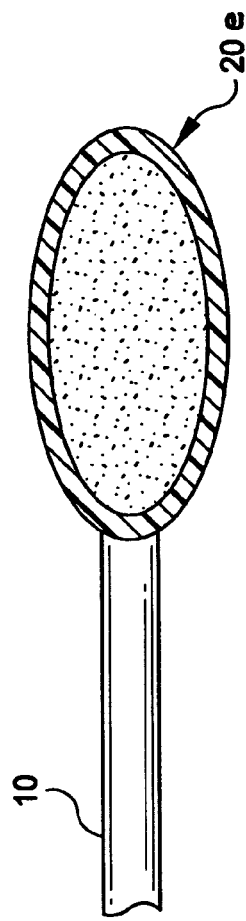

FIGS. 8–13 illustrate various embodiments of the distal tip 20. FIG. 8 shows an arrowhead distal tip 20. FIG. 9 shows a solid monolithic distal tip 20. FIG. 10 shows a hollow distal tip 20. FIG. 11 shows a composite distal tip 20. FIG. 12 shows a biostable polymer core 24 and bioabsorbable or dissolvable outer layer or shell 26. The shell 26 may be equidistantly centered about a core 24 or the shell 26 may be off-centered about the core 24 as shown. The core 24 may be partially disposed in the tubular body 10. FIG. 13 shows a distal tip 20 made of a porous biostable polymer material filled with a bioabsorbable or dissolvable material.

Figure 14:
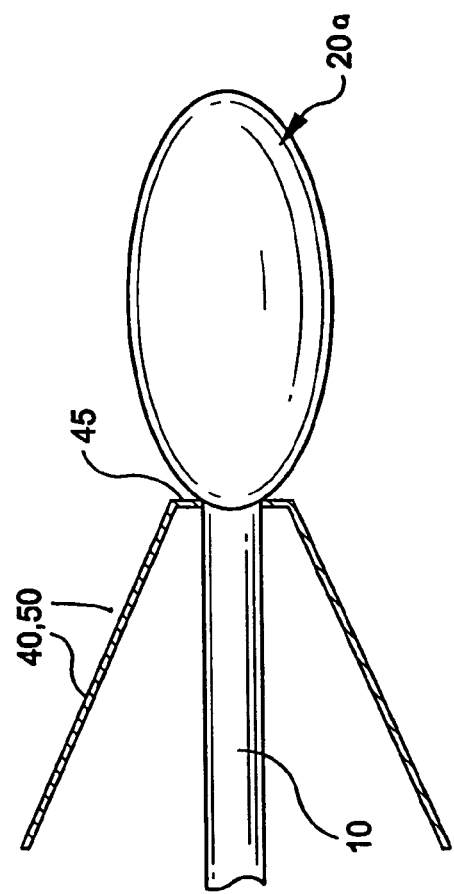
FIG. 14 is a schematic view of a distal tip attached on a tubular body and located distal of a deployed occlusion device.

FIG. 14 illustrates a distal tip 20 made of a solid bioabsorbable or dissolvable material on a tubular body 10. The distal tip 20 is located distal of a deployed occlusion device 50.

Figure 15:
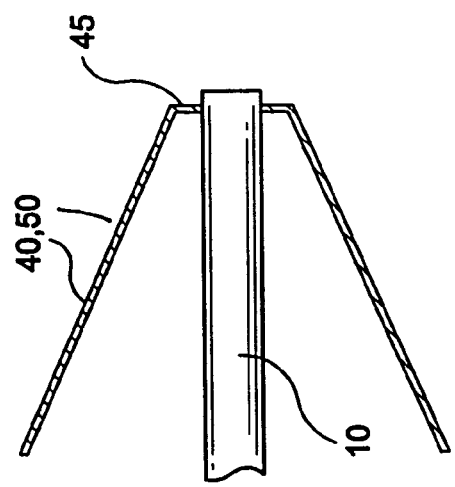
FIG. 15 is a schematic view of the tubular body after the distal tip has dissolved or bioabsorbed.

FIG. 15 illustrates a view of the tubular body 10 after the bioabsorbable or dissolvable material of the distal tip 20 has dissolved or bioabsorbed into the body. The tubular body 10 has a diameter small enough to pass in a proximal direction through an opening in the occlusion device 50.

Figure 16:
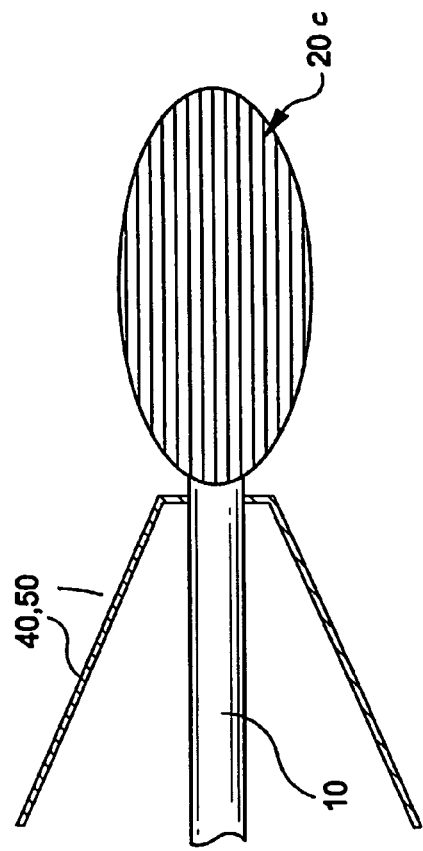
FIG. 16 is schematic view of a distal tip on a tubular body and located distal of a deployed occlusion device.

FIG. 16 illustrates a distal tip 20 made of a composite bioabsorbable or dissolvable material on a tubular body 10. The distal tip 20 is located distal of a deployed occlusion device 50.

Figure 17:
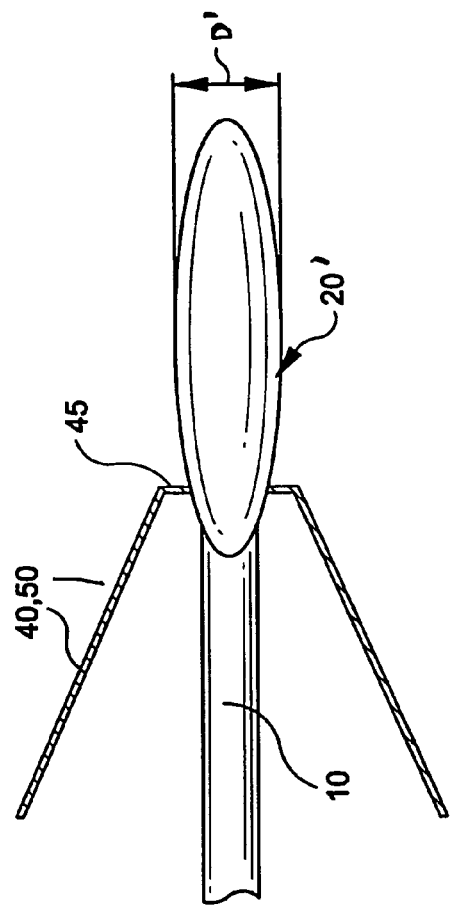
FIG. 17 is a schematic view of the distal tip after the distal tip has partially dissolved.

FIG. 17 illustrates a tubular body 10 and distal tip 20 after the bioabsorbable or dissolvable material in the distal tip 20' has dissolved or bioabsorbed into the body. The distal tip 20' has a sufficient dimension D' to pass in a proximal direction through an opening in the occlusion device 50.

Figure 18:
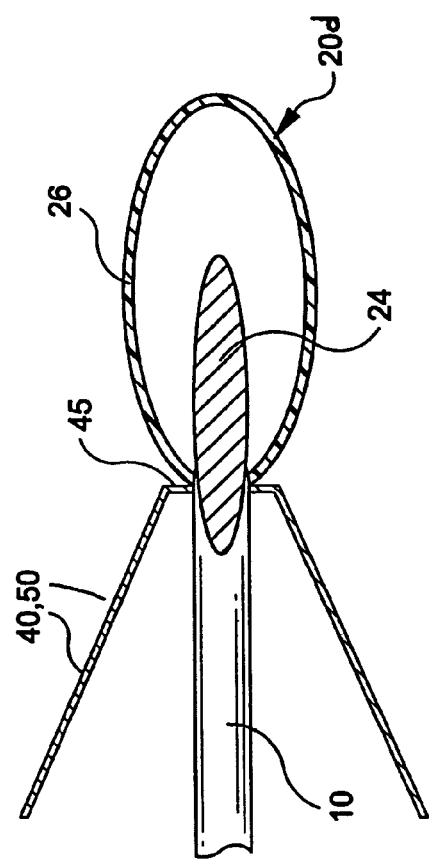
FIG. 18 is schematic view of a distal tip made of a core and an outer layer shell on a tubular body and located distal of a deployed occlusion device.

FIG. 18 illustrates a distal tip 20 made of an biostable polymer core 24 and a bioabsorbable or dissolvable material shell 26 disposed on a tubular body 10. The distal tip 20 is shown generally distal of a deployed occlusion device 50 other than the core 24 which is partially proximal of a member 45 and attached to the tubular body 10.

Figure 19:
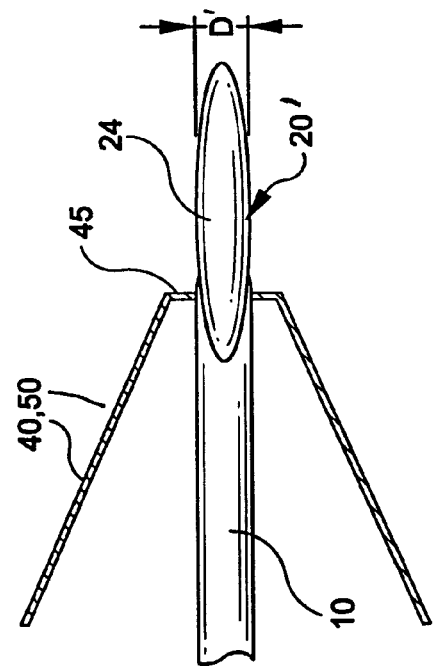
FIG. 19 is a schematic view of the tubular body and distal tip after the outer layer shell has dissolved.

FIG. 19 illustrates the tubular body 10 and distal tip 20' after the bioabsorbable or dissolvable material has dissolved. The distal tip 20' has a sufficient dimension D' to pass in a proximal direction through the occlusion device 50.

Figure 20:
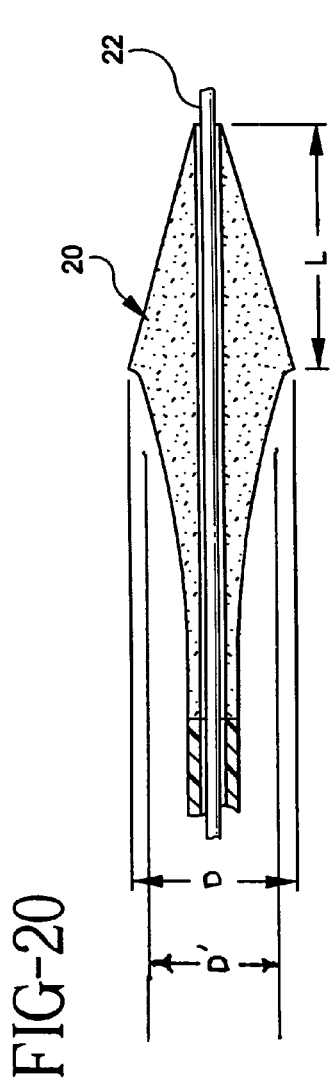
FIGS. 20–21 are schematic views of embodiments of the distal tip showing dimensions.
Figure 21:
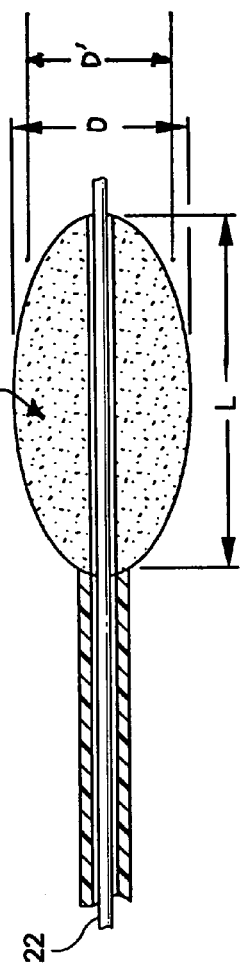

FIGS. 20–21 illustrates the distal tip 20 with manufactured dimension D and dimension D' after conversion to a lower profile via deformation, dissolving, or bioabsorption. The length L refers to a manufactured length and L' refers to converted shape. The dimensions D and D' are of the most importance. The dimension D' must be small enough to pass through member 45 or an opening in the occlusion device 50 when withdrawn from a body lumen.

The maximum profile manufactured dimension or diameter, D, of the distal tip 20 is about 1.00 to about 3.63 mm. The deformed, bioabsorbed or dissolved, partially bioabsorbed or partially dissolved tip diameter, D', can range from about zero to 2.54 mm, as indicated in the table below. The manufactured length, L, of the distal tip 20 is about 2–10 mm. The deformed length, L', of the distal tip 20, as it is being pulled through the occlusion device 45, can range from about zero to about four times the manufactured length L. Other manufactured sizes of the distal tip 20 are envisioned. For example, the distal tip 20 may be made with dimensions, D, of up to about a 6 mm, and length, L, from about 10 mm to about 50 mm.

Bioabsorption is the process by which the polymer undergoes strength degradation and mass degradation and the degradation products are metabolized or excreted by normal body functions. A bioabsorbable distal tip 20 may not entirely progress through a complete bioabsorption process before it changes to a smaller profile, D', and before it is withdrawn through a deployed occlusion device 50. The bioabsorbable distal tip 20 may undergo strength degradation in vivo which makes the polymer more easily deformable. Thus, less pulling force is required to squeeze the degraded polymer tip 20' through the lumen of the member 45 if the polymer yield strength or the Young's modulus is reduced by degradation and the polymer is less stiff or less strong from the degradation process. Less pulling force on the delivery system during withdrawal of the tubular body 10 is desired. As the bioabsorbable polymer in the distal tip 20' progresses through strength and mass degradation while in vivo, the volume of the distal tip 20' generally becomes smaller from the material loss.

Preferred embodiments of the distal tip 20, 20' are shown in the following table:

| Tip Design: | Material: | Max. Profile D at Manufacture Ø, Fr (mm) | Max. Profile D' After Tip Deforms, Dissolves Or Bio-absorbs, mm |
|---|---|---|---|
| Ellipse, Arrowhead or Diamond Shape Solid | Biostable Polymer, Bioabsorbable or Dissolvable Polymer | 11 (3.63) | 2.54 |
| | | 10 (3.33) | 2.33 |
| | | 9 (3.00) | 2.10 |
| | | 8 (2.65) | 1.86 |
| | | 7.5 (2.54) | 1.78 |
| | | 7 (2.32) | 1.62 |
| | | 6 (2.00) | 1.40 |
| | | 5 (1.67) | 1.17 |
| | | 4 (1.34) | 0.94 |
| | | 3 (1.00) | 0.70 |
| Ellipse, Arrowhead or Diamond Shape Hollow or Cavity | Biostable Polymer, Bioabsorbable or Dissolvable Polymer | 11 (3.63) | 1.82 |
| | | 10 (3.33) | 1.67 |
| | | 9 (3.00) | 1.50 |
| | | 8 (2.65) | 1.33 |
| | | 7.5 (2.54) | 1.27 |
| | | 7 (2.32) | 1.16 |
| | | 6 (2.00) | 1.00 |
| | | 5 (1.67) | 0.84 |
| | | 4 (1.34) | 0.67 |
| | | 3 (1.00) | 0.50 |
| Ellipse, Arrowhead or Diamond Shape Composite | Biostable Polymer, Bioabsorbable or Dissolvable Polymer | 11 (3.63) | 1.82 |
| | | 10 (3.33) | 1.67 |
| | | 9 (3.00) | 1.50 |
| | | 8 (2.65) | 1.33 |
| | | 7.5 (2.54) | 1.27 |
| | | 7 (2.32) | 1.16 |
| | | 6 (2.00) | 1.00 |
| | | 5 (1.67) | 0.84 |
| | | 4 (1.34) | 0.67 |
| | | 3 (1.00) | 0.50 |
| Ellipse, Arrowhead or Diamond Shape Cored | Biostable Polymer Core, Bioabsorbable or Dissolvable Case | 11 (3.63) | 1.82 |
| | | 10 (3.33) | 1.67 |
| | | 9 (3.00) | 1.50 |
| | | 8 (2.65) | 1.33 |
| | | 7.5 (2.54) | 1.27 |
| | Biostable Polymer Case, Bioabsorbable or | 7 (2.32) | 1.16 |
| | | 6 (2.00) | 1.00 |
| | | 5 (1.67) | 0.84 |
| | Dissolvable Core | 4 (1.34) | 0.67 |
| | | 3 (1.00) | 0.50 |
| Ellipse, Arrowhead or Diamond Shape Porous | Biostable Polymer Matrix, Bioabsorbable or Dissolvable Filler | 11 (3.63) | 2.54 |
| | | 10 (3.33) | 2.33 |
| | | 9 (3.00) | 2.10 |
| | | 8 (2.65) | 1.86 |
| | | 7.5 (2.54) | 1.78 |
| | | 7 (2.32) | 1.62 |
| | | 6 (2.00) | 1.40 |
| | | 5 (1.67) | 1.17 |
| | | 4 (1.34) | 0.94 |
| | | 3 (1.00) | 0.70 |

Figure 22:
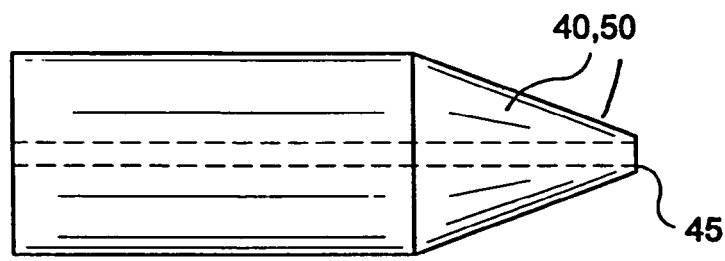
FIGS. 22–25A are schematic views of embodiments of the deployed occlusion device.
Figure 23:
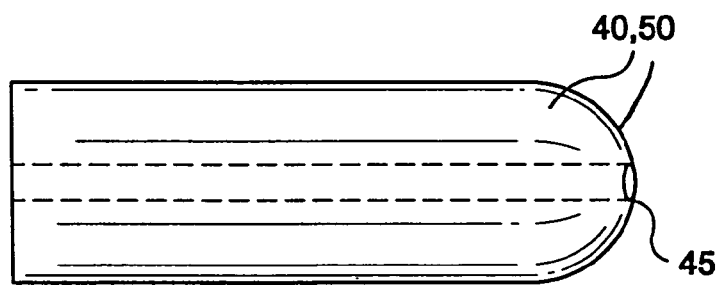
Figure 24:
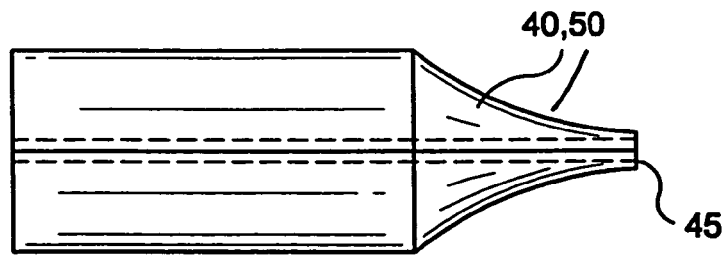
Figure 25A:
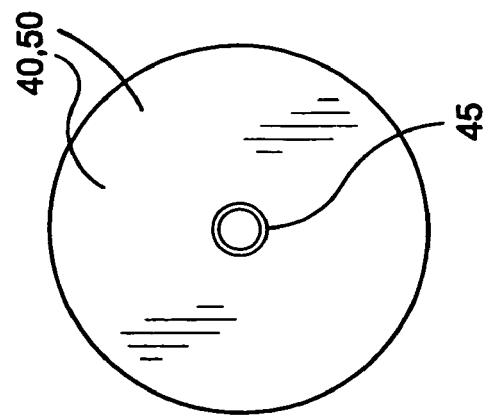
Figure 25:
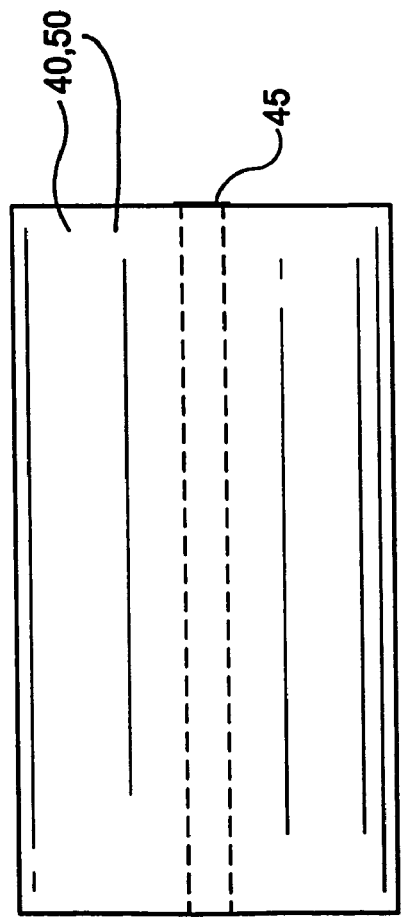

FIGS. 22–25 illustrate various embodiments of the deployed occlusion device 50. The advantage of the closed end is to prevent passage of emboli into the cranial arteriovenous system. FIG. 22 shows a truncated cone shape. FIG. 23 shows an elliptical shape. FIG. 24 shows a funnel shape. FIG. 25 shows a cylindrical shape. FIG. 25A is an end view of FIG. 25.

Figure 26:
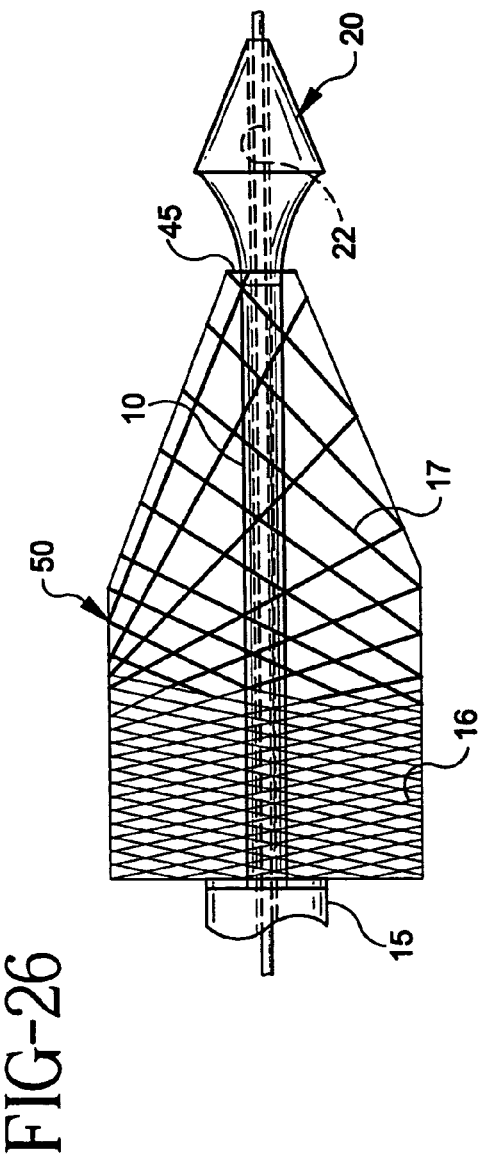
FIG. 26 is a schematic view of a deployed occlusion device and distal tip.

FIG. 26 illustrates a view of a deployed occlusion device 50 with member 45 and distal tip 20. Thrombogenically treated filaments 17 are shown on the occlusion device 50. An exterior tube 15 is used to constrain the occlusion device 50 on the tubular body 10. A guidewire lumen 22 is shown through the distal tip 20. The member 45 has an inner diameter larger than the tubular body 10 and smaller than the maximum profile of the distal tip 20. The outside diameter of the member 45 is less than about 5 mm and the inside diameter of the member 45 is less than about 3 mm. Member 45 may be made of a metal such as Elgiloy®, polymer material, or bioabsorbable material.

The occlusion device 50 has thrombogenic material 70 disposed on the filaments 16 or member 45. A thrombogenic treatment 70 including coating, fuzz, or fibers is disposed on a portion of one or more filaments 16 or the member 45 to enhance blood platelet adhesion which leads to vessel occlusion. Thrombogenic treatment 70 refers to the application of a material or altering a filament surface to affect the thrombogenicity. Coating refers to a material applied to the surface of the filament to form a film or layer on the filament surface. Thrombogenic treatment 70 may substantially encapsulate a plurality of ends of the filaments 16.

Figure 27:
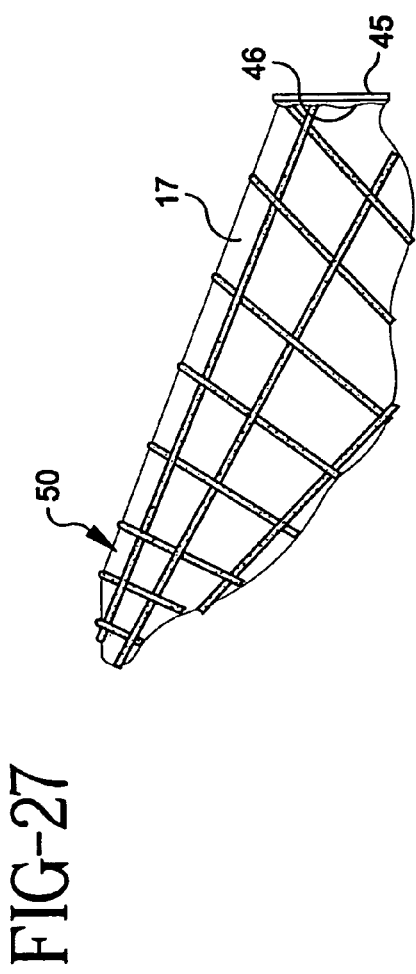
FIG. 27 is a cut-away schematic view of a portion of a deployed occlusion device with an attached member.

FIG. 27 illustrates a portion of the occlusion device 50 with treated filaments 17. Filaments 17 are shown attached to member 45. The member 45 is preferably made of metal or a polymer material and is attached by a weld or adhesive 46 to the ends of the filaments 16, 17. The filaments 16, 17 may also be attached to member 45 by bending or tying the filaments 16, 17 around the surface of the member, or the member 45 may have eyelets through which the filaments 16, 17 pass through and bend or tie to. This type of mechanical attachment would allow additional movement of the filaments 16, 17 at the distal end of the occlusion device 50 during constrainment on the delivery system 8 and during self-expansion. Member 45 may also be made from a thrombogenic treatment 70 formed at the end of filaments 16, 17.

Figure 28:
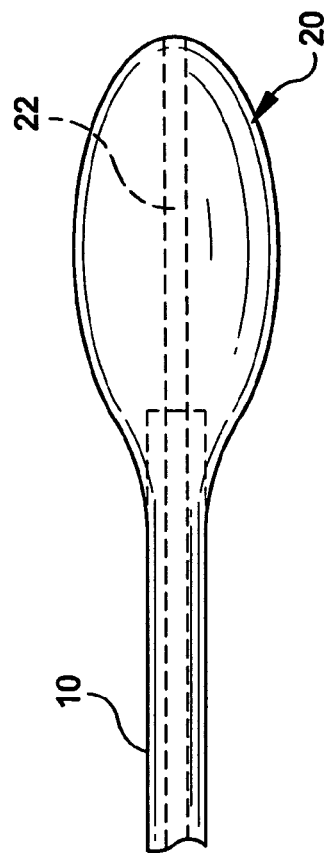
FIGS. 28–29 are schematic views of a distal tip on a tubular body.
Figure 29:
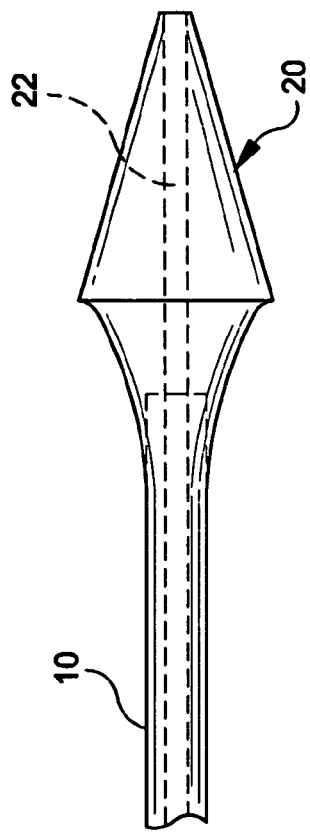

FIGS. 28–29 illustrate two embodiments of a distal tip 20. The distal tip 20 is firmly attached to the tubular body 10 and a substantially smooth transition is preferably formed at the intersection of parts 10, 20.

Figure 30:
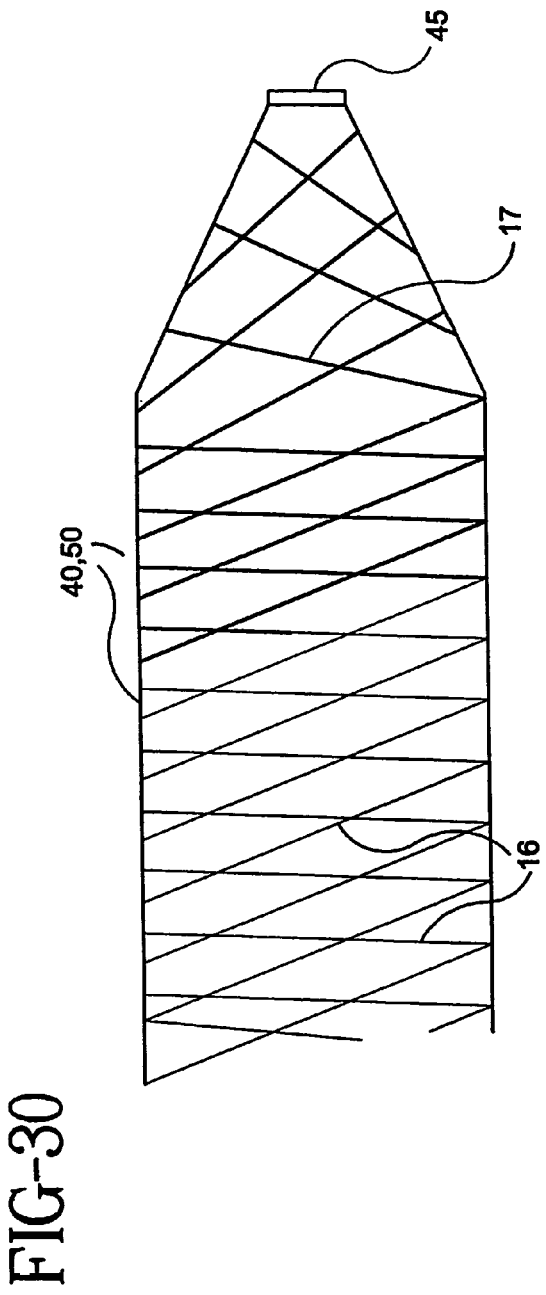
FIG. 30 is a schematic view of an occlusion device with thrombogenic material disposed on portions of filaments.
Figure 31:
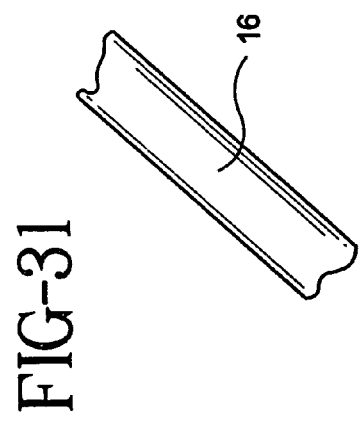
FIG. 31 is a schematic view of a bare filament.

FIG. 30 illustrates filaments 16, 17 forming an occlusion device 50. Thrombogenic material is disposed on filament 16 to form filament 17. The thrombogenic treatment 70 is preferably disposed on portions of filament 16 located at one end portion of the occlusion device 50, although thrombogenic treatment 70 of the surface of filament 16 may occur at various locations along the length of the occlusion device 50. The occlusion device 50 may have some bare filaments 16 as illustrated in FIGS. 30–31. A member 45 is shown attached at one end of the occlusion device 50.

Figure 32:
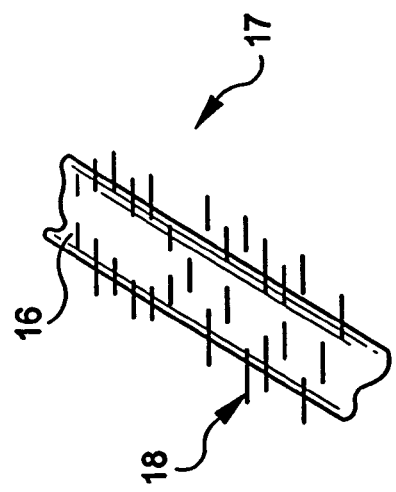
Figure 32A:
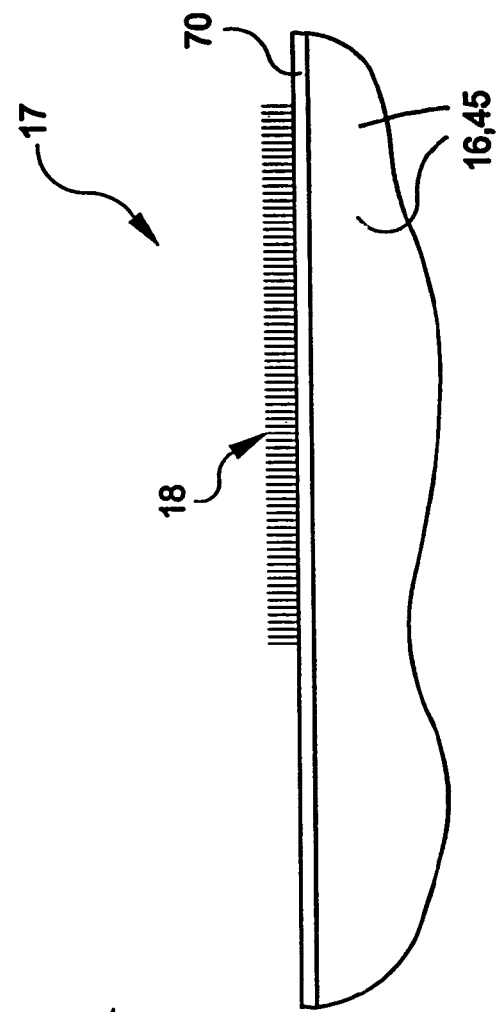
Figure 34:
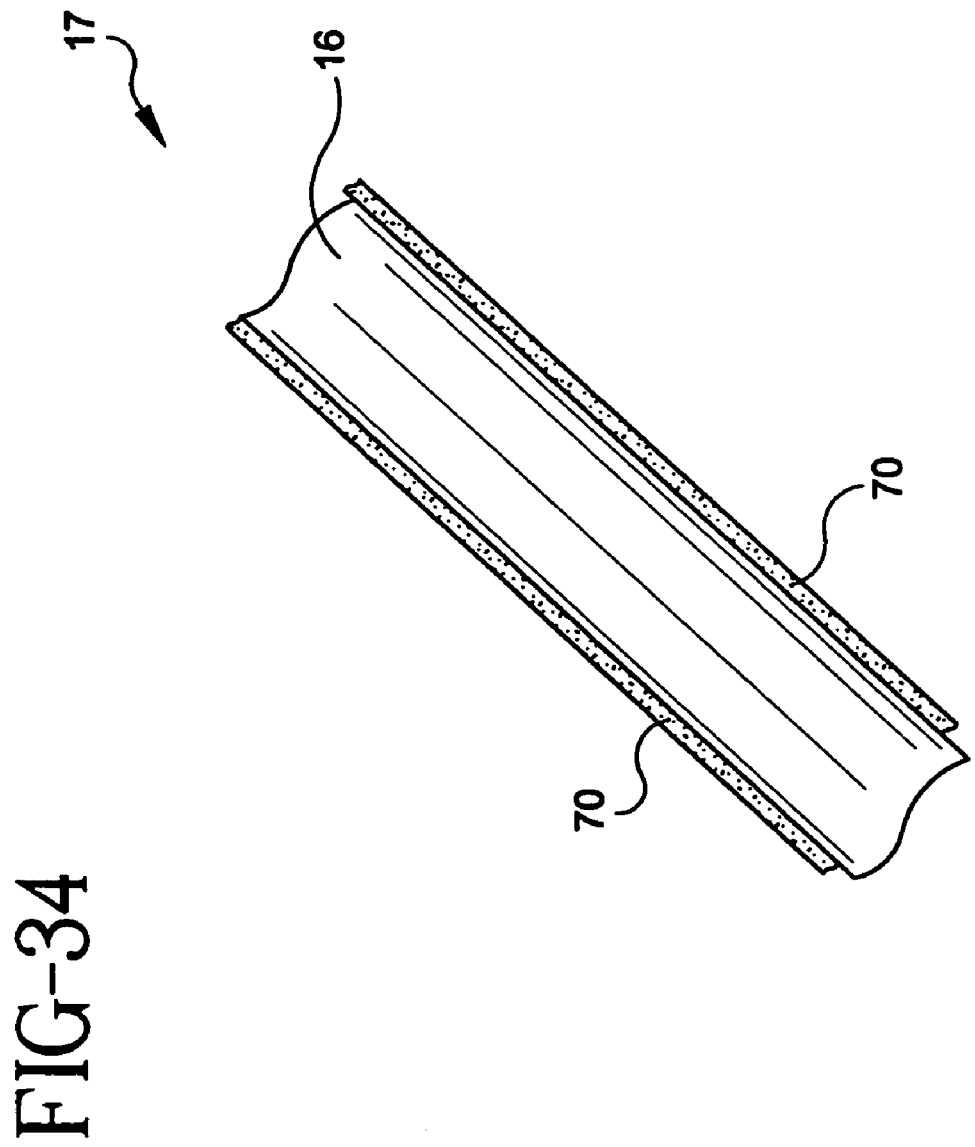
Figure 35:
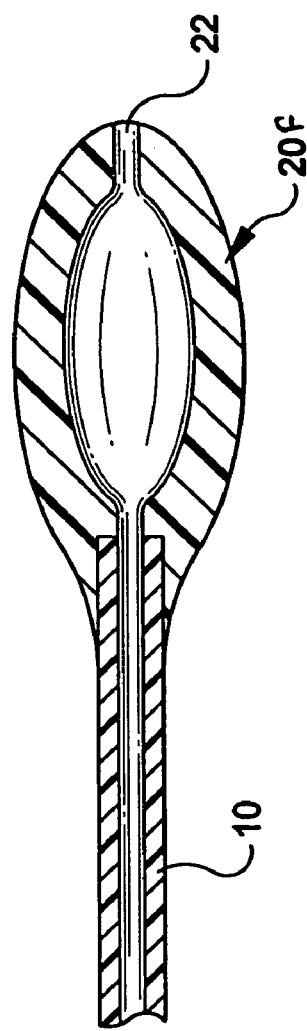
Figure 36:
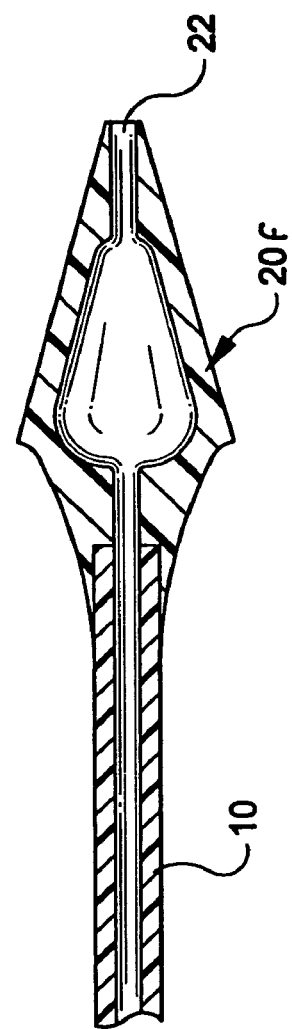
Figure 37:
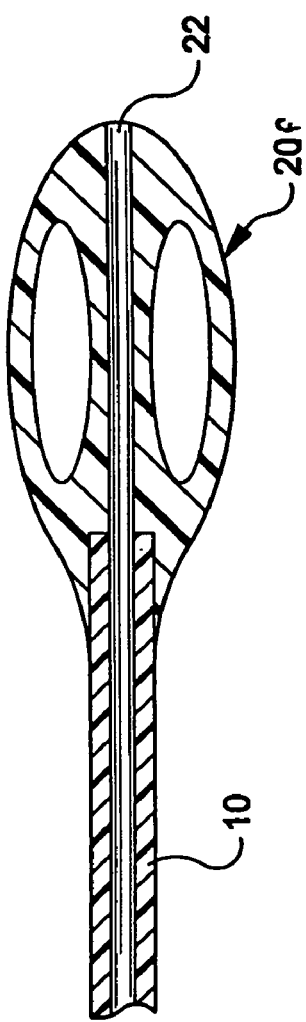
Figure 38:
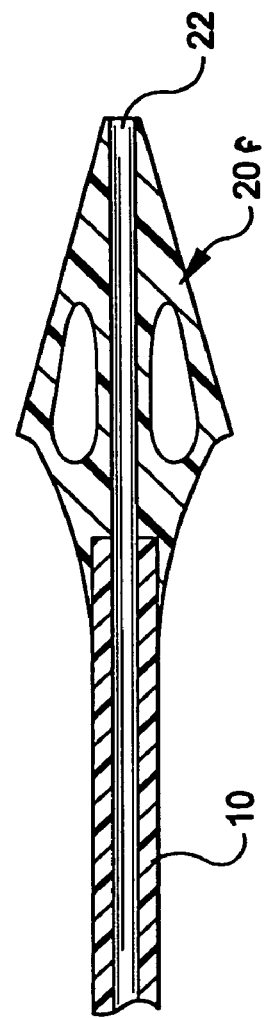
Figure 39:
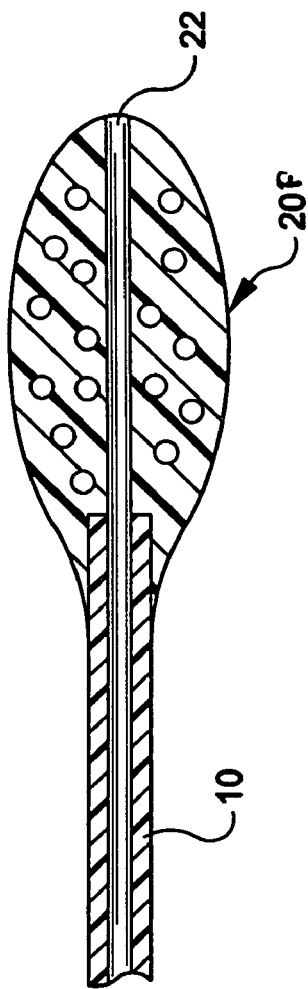
Figure 40:
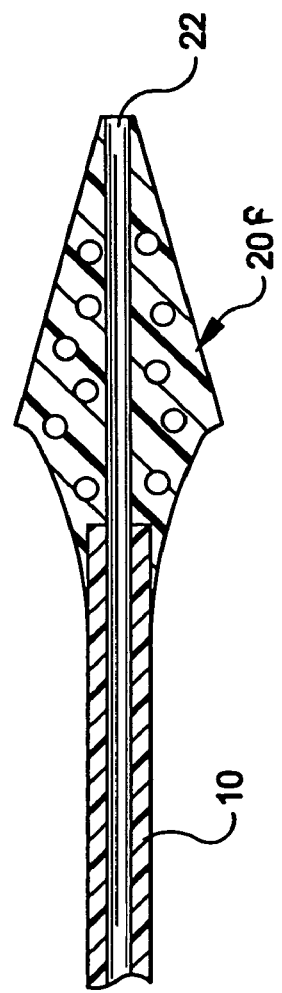

FIGS. 32–34 illustrate filament 17 including thrombogenic material such as fuzz or fiber or coating, respectively, disposed on filament 16. FIGS. 32A and 33A illustrate enlargements of the surface of filament 17 with a coating 70 and fuzz 18 and fibers 19, respectively. The fuzz 18 and fibers 19 are shown extending outward from coating 70 on the surface of the filament 16 or member 45 to enhance the thrombogenecity of the occlusion device 50.

The filaments 16 are treated to enhance thrombogenecity which advantageously reduces the time required for formation of thrombus 60 and vessel occlusion. The surface of the filament 16 may be coated with a material, such as silicone, which has a generally higher thrombogenicity than, for example, a smooth, bare Elgiloy® or stainless steel surface. Also, the layer or coating 70 may be made more thrombogenic by increasing the surface roughness or porosity. For example, the surface of the filament 16 may be coated with a polyurethane foam.

The thickness of a layer of the coating 70 on a filament 16 preferably ranges from about 100 angstroms to about 20 microns. The coating may be applied over one or portions of the longitudinal length of a filaments 16. The coating 70 may be applied over one or more portions of the longitudinal length of the endoprosthesis 40 or occlusion device 50. The coating 70 may cover all of the surface area of the filament 16 if the coating 70 is sufficiently weak or elastic and does not inhibit radial expansion and contraction of the endoprosthesis 40 or occlusion device 50. If the coating 70 is strong or stiff, filament crossing points may first be coated with a mold-release material to prevent adhesion of the thrombogenic coating 70. Alternatively, the filament crossing points may be masked with removeable tape or dissolvable material to prevent adhesion of the thrombogenic coating 70.

The thrombogenicity of the filaments 16 can be increased by adding synthetic or natural fuzz 18 or fibers 19 to the coating 70 before it cures so the fuzz or fiber network extends outward, preferably perpendicular or angular, from the surface of the filament 16 into the body lumen. The fizz 18 includes short, fine fibers (felt-like) which extend outward from the filament surface. The preferred average density of the fuzz 18 is about 40% to about 90% of the filament surface area portions that are desired to be covered by the fuzz 18, although average densities as low as 5% and up to about 95% are envisioned. The fibers 19 extend outward from the filament surface and include generally larger and longer fibers than the fuzz 18. The preferred average density of the fibers 19 is about 10% to about 60% of the filament surface area portions that are desired to be covered by the fibers 19, although average densities as low as 5% and up to about 95% are envisioned. The fuzz 18 or fibers 19 preferably are disposed on one or more surface area portions of one or more filaments 16 that oppose the fluid flow in the body lumen.

It is not necessary that the fuzz or fiber density is proportionally uniform about the circumference of the filament 16. Preferably, thrombogenic treatment 70 includes one or more filament surface area portions along the longitudinal length of the endoprosthesis 40 or occlusion device 50 that are exposed to fluid flow in the body lumen.

The fuzz 18 or fibers 19 act as attachment sites for blood platelets. Fuzz 18 is considered to be a tight grouping of very fine diameter fibers (less than 10 microns) with short lengths (less than 0.5 mm). Fibers 19 may be more occasionally distributed and have a diameter greater than about 10 microns and less than about 100 microns with lengths of about 0.5 to 10 mm. The fizz 18 or fibers 19 can be made of synthetic materials such as polyester (e.g., PET), polyurethane, nylon, or natural materials such as cotton or silk. Fuzz 18 or fibers 19 may be attached to the filaments 16 without the use of a coating 70 by tying or wrapping or they may be adhered with a biocompatible adhesive such as silicone, polyurethane, or cyanoacrylate.

FIGS. 35–40 illustrate various embodiments of the distal tip 20 having hollow, cavity or porous portions. An elastically deformable distal tip 20 with hollow, cavity or porous portions would be more easily deformed than a solid distal tip 20. The distal tip 20 may be made in various shapes and preferably a generally smooth transition occurs at the tubular body 10. The distal tip 20 preferably has a lumen 22 through the longitudinal axis although certain embodiments of the distal tip 20 may not have a lumen 22.

FIG. 41 illustrates a deployed occlusion device 50 with a member 45 attached at an end. FIG. 42 is a view of a deployed occlusion device 50 with thrombogenic treatment 70 on ends of the filaments 16.

Examples of the occlusion device 50 and delivery system 8 are as follows:

EXAMPLE 1

An occlusion device 50 for 4–5 mm diameter intracranial vessels can be made by braiding 20 strands of 0.10 mm diameter clad composite Elgiloy case/platinum core wire filaments 16 into a tubular mesh of helical coils on a 6.5 mm diameter steel bar and age hardening the braid in a vacuum heat treat furnace at 520–550° C. for 3 hours while axially stretched on a 6.0 mm diameter stainless steel tube. The heat treated occlusion device 50 is mounted on a mandrel having the shape of the occlusion device 50 (straight tubular section and conical section) and a metal ring 45 is welded onto the distal end. The inner diameter of the metal ring 45 is larger than the outer diameter of the tubular body 10 of the delivery system 8 and the outer diameter of the metal ring 45 is smaller than the inner diameter of the exterior tube 15 of the delivery system 8. The filaments 16 in the conical section and in a portion of the connecting straight tubular section are coated with a polymer such as polyurethane or silicone to make a microscopic rough "pebble grain" surface to increase thrombogenicity.

The delivery system 8 can be made of a 6 or 7 French size retractable sleeve design and includes a collapsible or elastically deformable distal tip 20. The distal tip 20 can be a hollow polyethylene molded shape that overlaps the tubular body 10 of the delivery system 8 by about 50% of the length of the constrained occlusion device 50. The occlusion device 50 can be loaded onto the delivery system 8 with the straight tubular section against the proximal end of the delivery system 8 and the conical section against the distal end of the delivery system 8.

EXAMPLE 2

The occlusion device 50 can be made substantially as described above in example 1.

The delivery system 8 can be made of a 6 or 7 French size retractable sleeve design with a dissolvable or bioabsorbable distal tip 20. The distal tip 20 can be molded from the same material found in gel-capsule pill casings. The material of the distal tip 20 can be compounded with a non-toxic radiopaque agent so that the dissolving process can be monitored with fluoroscopy to indicate when the delivery system 8 can be removed from the occlusion device 50. The distal tip 20 can overlap the tubular body 10 of the delivery system 8 by about 50% of the length of the constrained occlusion device 50. The occlusion device 50 can be loaded onto the delivery system 8 with the straight tubular section against the proximal end of the delivery system 8 and the conical section against the distal end of the delivery system 8.

EXAMPLE 3

An occlusion device 50 for 4–5 mm diameter intracranial vessels can be made by braiding 20 strands of 0.20 mm diameter highly oriented PET, absorbable suture filament 16, or PLLA filament 16 on an 8 mm diameter bar. At least 3 strands of the filament 16 in the braid are compounded with tantalum powder for radiopacity, or tantalum or platinum beads or rings are attached to the crossing points of the filaments 16. The braid is annealed on a 7 mm diameter tubular mandrel. A polymer ring 45 is attached to the distal end of the occlusion device 50. The filaments 16 are coated with a polymer such as polyurethane or silicone to make a rough "pebble grain" surface to increase thrombogenicity.

The delivery system 8 can be made of a 7 or 8 French size retractable sleeve design and includes a collapsible or elastically deformable distal tip 20. The distal tip 20 can be a hollow polyethylene molded shape that overlaps the tubular body 10 of the delivery system 8 by about 50% of the length of the constrained occlusion device 50. The occlusion device 50 can be loaded onto the delivery system 8 with the straight tubular section against the proximal end of the delivery system 8 and the conical section against the distal end of the delivery system 8.

EXAMPLE 4

The occlusion device 50 can be made substantially as described above in examples 1–3. One end of the occlusion device 50 can be substantially joined together, for example, by welding or adhesive 46 to form a closed end. The tubular body 10 of the delivery system 8 can pass through an interstitial open-space in the occlusion device 50. The distal tip 20 can have a lower profile dimension D' by having hollow portions and using a thin wall. A bioabsorbable or dissolvable distal tip 20 is preferred.

EXAMPLE 5

The occlusion device 50 can be made as described above in examples 1–4. The conical end and a portion of the connecting straight-tubular end can be coated with generally short fizz 18 or fibers 19 made of a polymer material. An adhesive of silicone or polyurethane can be used for attachment to the filament 16.

EXAMPLE 6

The occlusion device 50 can be made as described above in examples 1–5. The conical end and a portion of the connecting straight-tubular end can include a thrombogenic treatment 70 such as a drug or material that enhances blood platelet adhesion and thrombus formation on the filaments 16, 17.

While a particular preferred embodiment has been illustrated and described, the scope of protection sought is in the claims that follow.

What is claimed is:

1. An occlusion device delivery system comprising:
    a catheter including an elongated shaft having a distal portion and a distal extremity;
    a releasably deployable occlusion device positioned on the distal portion of the elongated shaft; and
    a distal tip member immovably secured to the distal portion of the elongated shaft, wherein the distal tip member distally extends beyond the distal extremity of the elongated shaft, the distal tip member including at least a partially bioabsorbable or dissolvable material.

2. The delivery system of claim 1, wherein the distal tip member further comprises a guidewire lumen.

3. The delivery system of claim 1, wherein the distal tip member is solid.

4. The delivery system of claim 1, wherein the distal tip member is configured to bioabsorb or dissolve in less than about 15 minutes in vivo.

5. The delivery system of claim 1, wherein the distal tip member is configured to bioabsorb or dissolve within a range of about 5 to about 10 minutes in vivo.

6. The delivery system of claim 1, wherein the distal tip member is configured to either bioabsorb or dissolve to a smaller profile.

7. The delivery system of claim 6, wherein the distal tip member is configured to remain disposed on the distal portion of the elongated shaft during the entire bioabsorption or dissolution process.

8. The delivery system of claim 6, wherein the occlusion device comprises a distal opening when deployed, and the distal tip member, in the smaller profile, is configured to proximally pass through the distal opening of the deployed occlusion device when the elongated shaft is displaced in a proximal direction.

9. The delivery system of claim 1, wherein the distal tip member is configured to bioabsorb or dissolve substantially away.

10. The delivery system of claim 1, wherein the distal tip member has a substantially smooth transition at an edge of the elongated shaft.

11. The delivery system of claim 1, wherein the occlusion device is self-expanding.

12. The delivery system of claim 1, wherein the occlusion device is a stent.

13. The delivery system of claim 1, wherein the elongated shaft is a flexible catheter body.

14. The delivery system of claim 1, wherein the distal tip member is configured for not sliding off of the tubular body during the bioabsorption or dissolution process.

15. The delivery system of claim 1, wherein the distal tip member is configured for remaining intact during the bioabsorption or dissolution process.

16. An occlusion device delivery system comprising:
    a catheter including an elongated shaft having a distal portion;

a releasably deployable occlusion device positioned on the distal portion of the elongated shaft; and a distal tip member immovably secured to the distal portion of the elongated shaft, the distal tip member configured to undergo bioabsorption or dissolution when the distal tip member is placed in vivo, wherein the distal tip member is configured to remain immovably secured to the distal portion of the elongated shaft during the entire bioabsorption or dissolution process, wherein the distal tip member does not hinder deployment of occlusion device prior to undergoing bioabsorption or dissolution.

17. The delivery system of claim 16, wherein the distal tip member further comprises a guidewire lumen.

18. The delivery system of claim 16, wherein the distal tip member is solid.

19. The delivery system of claim 16, wherein the distal tip member is configured to bioabsorb or dissolve in less than about 15 minutes in vivo.

20. The delivery system of claim 16, wherein the distal tip member is configured to bioabsorb or dissolve within a range of about 5 to about 10 minutes in vivo.

21. The delivery system of claim 16, wherein the distal tip member is configured to either bioabsorb or dissolve to a smaller profile.

22. The delivery system of claim 21, wherein the occlusion device comprises a distal opening when deployed, and the distal tip member, in the smaller profile, is configured to proximally pass through the distal opening of the deployed occlusion device when the elongated shaft is displaced in a proximal direction.

23. The delivery system of claim 16, wherein the distal tip member is configured to bioabsorb or dissolve substantially away.

24. The delivery system of claim 16, wherein the distal tip member has a substantially smooth transition at an edge of the elongated shaft.

25. The delivery system of claim 16, wherein the occlusion device is self-expanding.

26. The delivery system of claim 16, wherein the occlusion device is a stent.

27. The delivery system of claim 16, wherein the elongated shaft is a flexible catheter body.

28. The delivery system of claim 1, wherein the distal tip member is configured for not sliding off of the tubular body during the bioabsorption or dissolution process.

29. The delivery system of claim 1, wherein the distal tip member is configured for remaining intact during the bioabsorption or dissolution process.

30. An occlusion device delivery system comprising:

a catheter including an elongated shaft having a distal portion;

a releasably deployable occlusion device positioned on the distal portion of the elongated shaft, the occlusion device comprising a distal opening when deployed; and a distal tip member immovably secured to the distal portion of the elongated shaft distal to the occlusion device, the distal tip member configured to either bioabsorb or dissolve to a smaller profile when the distal tip member is placed in vivo, wherein the distal tip member is configured to remain immovably secured to the distal portion of the elongated shaft during the entire bioabsorption or dissolution process, so that the distal tip member may proximally pass through the distal opening of the deployed occlusion device when the elongated shaft is displaced in a proximal direction.

31. The delivery system of claim 16, wherein the distal tip member further comprises a guidewire lumen.

32. The delivery system of claim 16, wherein the distal tip member is solid.

33. The delivery system of claim 16, wherein the distal tip member is configured to bioabsorb or dissolve to the smaller profile in less than about 15 minutes in vivo.

34. The delivery system of claim 16, wherein the distal tip member is configured to bioabsorb or dissolve to the smaller profile within a range of about 5 to about 10 minutes in vivo.

35. The delivery system of claim 16, wherein the distal tip member has a substantially smooth transition at an edge of the elongated shaft.

36. The delivery system of claim 16, wherein the occlusion device is self-expanding.

37. The delivery system of claim 16, wherein the occlusion device is a stent.

38. The delivery system of claim 16, wherein the elongated shaft is a flexible catheter body.

39. The delivery system of claim 30, wherein the distal tip member is configured for not sliding off of the tubular body during the bioabsorption or dissolution process.

40. The delivery system of claim 30, wherein the distal tip member is configured for remaining intact during the bioabsorption or dissolution process.

* * * * *